(12) United States Patent
Normand et al.

(10) Patent No.: US 11,395,632 B2
(45) Date of Patent: Jul. 26, 2022

(54) IMPLEMENTABLE SEMICONDUCTOR DEVICE, COMPRISING AN ELECTRODE AND CAPACITOR, AND CORRESPONDING MANUFACTURING METHOD

(71) Applicant: Murata Manufacturing Co., Ltd., Nagaokakyo (JP)

(72) Inventors: Nicolas Normand, Herouville Saint Clair (FR); Stéphane Bouvier, Cairon (FR)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 144 days.

(21) Appl. No.: 16/591,870

(22) Filed: Oct. 3, 2019

(65) Prior Publication Data
US 2020/0107783 A1   Apr. 9, 2020

(30) Foreign Application Priority Data

Oct. 4, 2018 (EP) ..................................... 18306308

(51) Int. Cl.
| | |
|---|---|
| *A61N 1/00* | (2006.01) |
| *A61B 5/00* | (2006.01) |
| *A61N 1/05* | (2006.01) |
| *A61N 1/36* | (2006.01) |
| *H01L 27/08* | (2006.01) |
| *H01L 29/66* | (2006.01) |
| *H01L 29/94* | (2006.01) |
| *A61B 18/00* | (2006.01) |

(52) U.S. Cl.
CPC .......... *A61B 5/6867* (2013.01); *A61B 5/0031* (2013.01); *A61N 1/0534* (2013.01); *A61N 1/3605* (2013.01); *H01L 27/0805* (2013.01); *H01L 29/66181* (2013.01); *H01L 29/945* (2013.01); *A61B 2018/00315* (2013.01)

(58) Field of Classification Search
CPC ......... A61B 5/6867; A61B 5/25; A61B 5/263; A61B 5/277; A61B 5/0031; A61B 2018/00315; A61N 1/0534; A61N 1/3605; A61N 1/05; A61N 1/0529; A61N 1/0551; A61N 1/056; A61N 1/04–06; H01L 27/0805; H01L 29/66181; H01L 29/945
See application file for complete search history.

(56) References Cited

U.S. PATENT DOCUMENTS

| | | | |
|---|---|---|---|
| 8,283,750 B2 | 10/2012 | Guiraud et al. | |
| 2006/0154436 A1* | 7/2006 | Kim | ........................ H01L 28/65 438/396 |
| 2014/0214129 A1* | 7/2014 | Waataja | ............. A61N 1/36007 607/59 |
| 2014/0277316 A1* | 9/2014 | Chen | ........................ A61N 1/05 607/116 |
| 2019/0212319 A1* | 7/2019 | Voiron | ............... G01N 33/4836 |

FOREIGN PATENT DOCUMENTS

WO   WO-2018050887 A1 *  3/2018  ........... H01L 29/945

* cited by examiner

*Primary Examiner* — Scott M. Getzow
(74) *Attorney, Agent, or Firm* — ArentFox Schiff LLP (57) ABSTRACT

The invention concerns an implementable semiconductor device that includes an electrode configured to be in contact with biological tissue and at least one capacitor, and wherein the capacitor includes a capacitor electrode having a first surface facing and in contact with the electrode configured to be in contact with biological tissue.

16 Claims, 5 Drawing Sheets

IMPLEMENTABLE SEMICONDUCTOR DEVICE, COMPRISING AN ELECTRODE AND CAPACITOR, AND CORRESPONDING MANUFACTURING METHOD

CROSS REFERENCE TO RELATED APPLICATIONS

The present application claims priority to European Patent Application No. 18 306308.0, filed on Oct. 4, 2018, the entire contents of which are incorporated herein by reference.

FIELD OF THE INVENTION

The present invention relates to the field of integration and, more particularly, to implantable semiconductor devices.

The present invention more precisely relates to implantable electronic devices having an electrode configured to be in contact with biological tissue.

TECHNICAL BACKGROUND

Implementable semiconductor devices may be inserted in a human or animal body so as to be in contact with biological tissue (a portion of a human or animal body). Typically, these devices comprise an electrode to provide an electrical contact between the device and the biological tissue. The dimensions and geometry of the electrodes may be chosen so as to optimize the quality of the sensed signals, if signals are sensed.

The electrode may then be used for sensing electrical signals in the biological tissue or also for stimulating the biological tissue. Typically, the electrodes receive signals that are processed by an electronic circuit, or emit signals that have been generated by an electronic circuit. These electronic circuits may comprise, by way of example, a processor.

It is conceivable to the person skilled in the art that these implantable electronic devices have to be biocompatible and that this requirement extends to the electronic circuits and to the electrodes. This implies restrictions on the materials that may be used but also on the electrical functions of the device. Means for preventing continuous voltages from appearing in the body in which the implementable semiconductor device is implemented are usually required.

For example, it has been proposed to use a DC block connected between the electrode and the electronic circuit. This DC block is typically implemented using a capacitor. In order to perform the expected function, the capacitor is required to have a large capacitance value. The capacitor has to be able to ensure electrical isolation even if an electrical failure appears. Typically, the capacitance values of these capacitors are of the order to several tens of nanofarads, this leads to a difficulty in integrating the capacitors which are bulky.

In order to accommodate a bulky is solved by placing the capacitors on a printed circuit board along with the electrodes and the electronic circuits. On this printed circuit board, the components such as the capacitors and the electrodes are connected using metal lines and placed in the vicinity of one another.

This solution is not satisfactory because there are still risks of continuous voltages coming from the external environment of the device and appearing at the level of the capacitor.

The present invention has been made in the light of the above problems.

SUMMARY OF THE INVENTION

The present invention provides an implementable semiconductor device, comprising an electrode configured to be in contact with biological tissue and at least one capacitor, wherein the capacitor comprises a capacitor electrode having a first surface facing and in (electrical) contact with the electrode configured to be in contact with biological tissue.

Thus, the electrode configured to be in contact with biological tissue and the capacitor electrode are in contact and are connected without using metal lines extending on a printed circuit board. The electrode configured to be in contact with biological tissue is formed on the first surface of the capacitor electrode.

The electrode configured to be in contact with biological tissue is arranged so as to face the first surface of the capacitor electrode, and the distance between the two is therefore minimized. This reduces the possibility of a continuous voltage generated in the external environment from being in contact with the electrode configured to be in contact biological tissue.

It should be noted that by "facing", what is meant is that the electrode configured to be in contact with biological tissue comprises a surface which faces and is in contact with the first surface of the capacitor electrode. Contact between the capacitor electrode and the electrode configured to be in contact with biological tissue may then be direct or indirect (for example if there is a layer of material between the two).

The first surface of the capacitor electrode is also substantially in the shape of the electrode configured to be in contact with biological tissue.

The above defined device is particularly suitable for deep brain stimulation, cardiac stimulation and spinal cord stimulation. For deep brain stimulation, miniaturization and high density are required to obtain more accuracy in the neuronal stimulation with less unwanted side effects. For cardiac stimulation, large area and custom shapes are required. For spinal cord stimulation, miniaturization is required to avoid sensitive area.

According to a particular embodiment, the electrode configured to be in contact with biological tissue comprises a layer of biocompatible conductive material facing said first surface of the capacitor electrode.

This layer of biocompatible conductive material may be deposited on the first surface of the capacitor electrode.

According to a particular embodiment, said capacitor electrode comprises a semiconductor region.

For example, the capacitor electrode may be a silicon substrate, preferably a doped silicon substrate. The remaining elements of the capacitor, an insulating layer and a second electrode, may be formed on this substrate on the side opposite to the one having the first surface facing and in contact with the electrode configured to be in contact with biological tissue.

According to a particular embodiment, the capacitor is a three-dimensional capacitor and the capacitor electrode comprises at least one of a pillar, a trench, or a hole, on a side opposite to the side having the first surface facing and in contact with the electrode configured to be in contact with biological tissue.

For example, if the capacitor electrode comprises a semiconductor region, or is in the form of a silicon substrate, the capacitor electrode may be etched to define pillars, trenches, or holes. These etched structures may be filled with an insulating layer and a conductive material forming the second electrode of the capacitor. This type of structure increases the surface area of the capacitor and consequently the capacitance.

Manufacturing of a three-dimensional capacitor is described, by way of example, in document U.S. Pat. No. 8,283,750.

It should be noted that the three-dimensional structures mentioned above (pillar, trench, hole) may be arranged in an array. This array may have substantially the shape of the electrode configured to be in contact with biological tissue.

According to a particular embodiment, the device comprises two stacked capacitors connected in series or in parallel, said capacitor electrode being an electrode of the two stacked capacitors.

By way of example, the two stacked capacitors may be an arrangement designated using the acronym MIMIM ("Metal Insulator Metal Insulator Metal").

For example, capacitors connected in parallel may be used to increase the capacitance density in the device.

Capacitors connected in series provide improved security because in the event of a failure of a capacitor, an open circuit may be maintained because there is still a functioning capacitor. Also, if a capacitor is short-circuited, the electrode configured to be in contact with biological tissue may still operate, but with an increased capacitance. This increased capacitance is detectable.

According to a particular embodiment, the electrode configured to be in contact with biological tissue comprises a conductive material chosen in the group comprising gold, nickel, tungsten, platinum, palladium, cobalt, or an alloy of at least two materials of the group of conductive materials.

According to a particular embodiment, the device comprises an encapsulating layer comprising an insulating material chosen in the group comprising alumina, parylene (poly(p-xylylene)), or a combination of at least two materials of the group of insulating material, the encapsulating layer being arranged to at least partially (or completely) encapsulate the capacitor and to leave uncovered at least the electrode configured to be in contact with biological tissue.

This encapsulating layer ensures that the only conductive area of the device which may be in contact with biological tissue is the electrode configured to be in contact with biological tissue.

According to a particular embodiment, the device comprises a plurality of electrodes configured to be in contact with biological tissue, each electrode configured to be in contact with biological tissue being associated with at least one capacitor comprising a capacitor electrode having a first surface facing and in contact with the electrode configured to be in contact with biological tissue.

By way of example, the plurality of electrodes configured to be in contact with biological tissue may be arranged in an array.

According to a particular embodiment, the device comprises trenches surrounding each electrode configured to be in contact with biological tissue and their associated at least one associated capacitor.

It should be noted that if the capacitor electrodes which have first surfaces in contact with an electrode configured to be in contact with biological tissue comprise a semiconductor substrate, then the trenches may extend in the entire thickness of this semiconductor substrate.

According to a particular embodiment, the trenches are empty or comprise an insulating material.

The invention also provides a method for manufacturing an implementable semiconductor device, comprising:

forming at least one capacitor comprising a capacitor electrode having a first surface, forming an electrode configured to be in contact with biological tissue facing and in contact with the first surface of the capacitor electrode.

This method may be used to manufacture all the embodiments of the implementable semiconductor device as defined above.

According to a particular embodiment, the method comprises depositing a layer of biocompatible conductive material on said first surface of the capacitor electrode.

According to a particular embodiment, the capacitor electrode comprises a semiconductor region.

According to a particular embodiment, the capacitor is a three-dimensional capacitor and forming the capacitor comprises forming at least one of a pillar, a trench, or a hole, on a side opposite to the side having the first surface facing and in contact with the electrode configured to be in contact with biological tissue.

According to a particular embodiment, the method comprises forming two stacked capacitors connected in series or in parallel, said capacitor electrode being an electrode of the two stacked capacitors.

According to a particular embodiment, forming the electrode configured to be in contact with biological tissue comprises depositing a layer of conductive material chosen in the group comprising gold, nickel, tungsten, platinum, palladium, cobalt, or an alloy of at least two materials of the group of conductive materials.

According to a particular embodiment, the method comprises forming an encapsulating layer comprising an insulating material chosen in the group comprising alumina, parylene, or a combination of at least two materials of the group of insulating material, the encapsulating layer being arranged to at least partially encapsulate the capacitor and to leave uncovered at least the electrode configured to be in contact with biological tissue.

According to a particular embodiment, the method comprises forming a plurality of electrodes configured to be in contact with biological tissue, each electrode configured to be in contact with biological tissue being associated with at least one capacitor comprising a capacitor electrode having a first surface facing and in contact with the electrode configured to be in contact with biological tissue.

According to a particular embodiment, the method comprises forming trenches surrounding each electrode configured to be in contact with biological tissue and their associated at least one associated capacitor.

According to a particular embodiment, the trenches comprise an insulating material or are empty.

BRIEF DESCRIPTION OF THE DRAWINGS

Further features and advantages of the present invention will become apparent from the following description of certain embodiments thereof, given by way of illustration only, not limitation, with reference to the accompanying drawings in which.

DETAILED DESCRIPTION OF EXAMPLE EMBODIMENTS

Different examples of implementable semiconductor devices and their associated manufacturing method will now be described.

Figure 1:
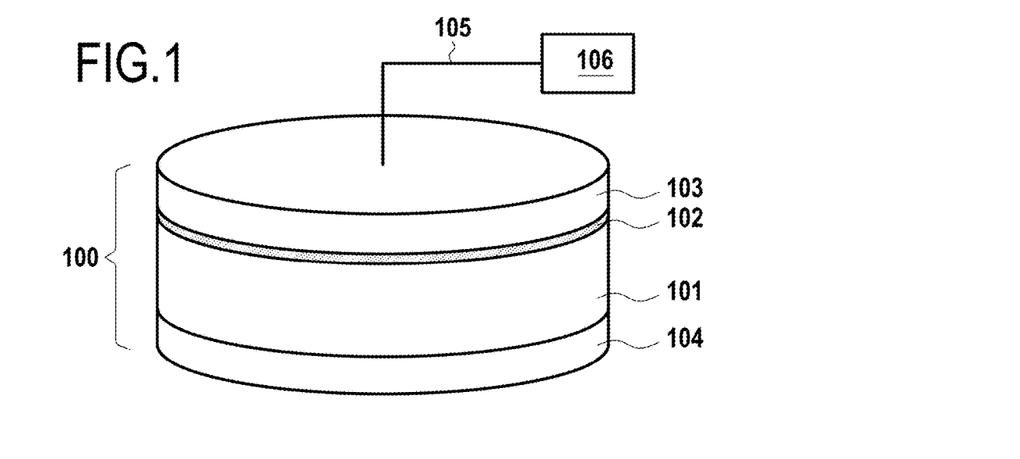
FIG. 1 is a perspective view of a device according to an example.

FIG. 1 is a perspective view of an implementable semiconductor device. This device may be a device suitable for deep brain stimulation, cardiac stimulation and spinal cord stimulation.

On this figure, a capacitor 100 has been represented. This capacitor comprises a bottom electrode 101 consisting, in this example, of a doped silicon substrate. On top of the bottom electrode 101, a dielectric layer 102 has been formed. This dielectric layer 102 may comprise silicon dioxide.

The capacitor 100 is also equipped of a top electrode 103, and this top electrode 103 may be, for example, a layer of conductive material deposited on the dielectric layer 102. In this example, the capacitor 100 is a two-dimensional planar capacitor.

In order to perform the above-mentioned functions, the capacitor 100 is equipped with an electrode 104 configured to be in contact with biological tissue. This electrode 104 comprises a layer of conductive material, chosen so as to be able to conduct electricity and which is biocompatible. By way of example, the electrode 104 comprises a conductive material chosen in the group comprising gold, nickel, tungsten, platinum, palladium, cobalt, or an alloy of at least two materials of the group of conductive materials.

The electrode 104 is deposited on the bottom surface of the bottom electrode 101. Therefore, these two electrodes are in electrical contact, and this electrical contact is direct in this example. Furthermore, it results from this deposition that the bottom surface of the bottom electrode 101 faces the electrode 104 configured to be in contact with biological tissue. Also, the two electrodes (or at least the bottom surface of electrode 101 and electrode 104) have substantially the same shape (circular in the illustrated example).

Thus, the security of the implementable device is improved because the distance between the electrode 104 and the electrode 101 is minimized.

In order to control the electrode 104 or to receive signals sensed by the electrode 104, the top electrode 103 of the capacitor 100 is connected, using a wired connection 105, to an electronic circuit 106 configured to perform the processing of the signals sensed or emitted by the electrode 104.

It should be noted that in the implementable devices of the prior art, the electrode configured to be in contact with biological tissue is connected to the associated capacitor using a wired connection on a printed circuit board. This is avoided in the above described example.

Figure 2:
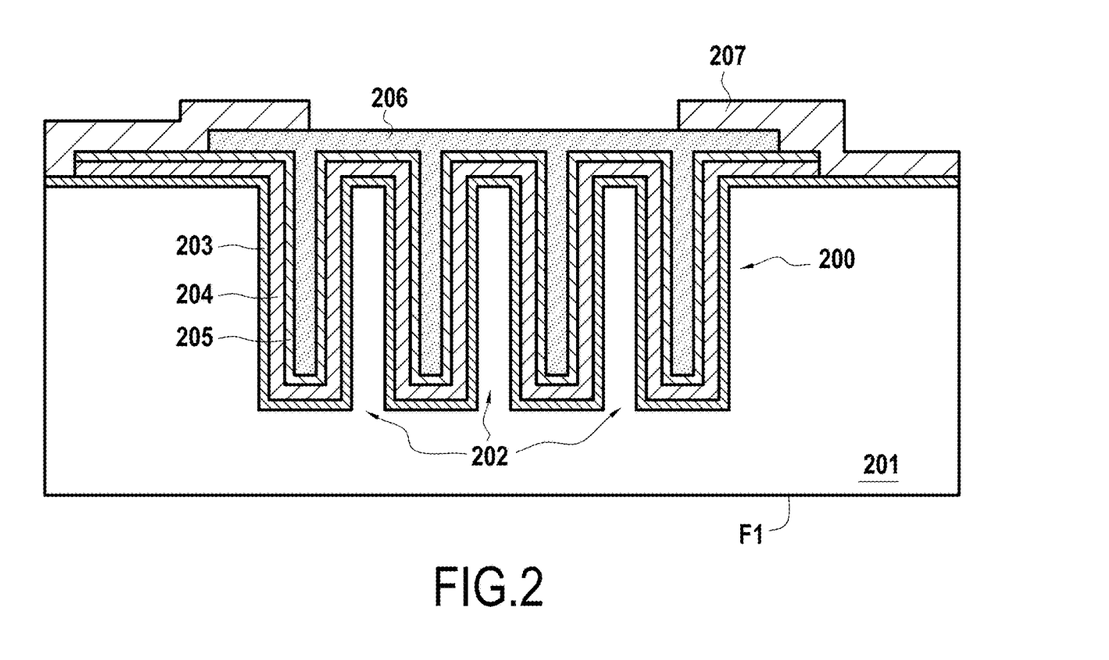
FIG. 2 is a side view of two capacitors on which an electrode according to the invention will be formed.

FIG. 2 is a side view of two stacked capacitors 200. The capacitors 200 are three-dimensional capacitors. In fact, the capacitors 200 are formed using a semiconductor substrate (for example a substrate comprising semi-conductive material, preferably comprising doped silicon) and this substrate is also the bottom electrode 201 of the stacked capacitors 200.

The bottom electrode 201 has been etched in order to form pillars 202, for example using the technique well known to the person skilled in the art as Deep Reactive Ion Etching (or DRIE). This method is particularly suitable to form high aspect ratio structures such as the pillars 202. This etching step forms the bottom electrode 201.

Then, a dielectric layer 203 is deposited in a conformal manner above and in-between the pillars 202.

An intermediary electrode 204 is also formed by deposition of conductive material in a conformal manner above and in-between the pillars 202 covered by the dielectric layer 203. A first capacitor is obtained.

In order to form a second capacitor, a second dielectric layer 205 is deposited in a conformal manner above and in-between the pillars 202 covered by the intermediary electrode 204.

This second dielectric layer 205 is then covered by a top electrode 206 which is formed by depositing conductive material so as to fill the trenches formed between the pillars 202. Two stacked capacitors connected in series are then obtained.

The top electrode 206 may be connected to an electronic circuit analogous to the electronic circuit 106 described in reference to FIG. 106. In fact, the embodiment of FIG. 1 and the embodiment of FIG. 2 are analogous except in that the planar capacitor of FIG. 1 is replaced by a three-dimensional stack of two capacitors on FIG. 2.

Additionally, it should be noted that a passivation layer 207 is deposited on top of the device while leaving the top electrode 206 at least partially uncovered.

In order to form an implantable semiconductor device, an electrode configured to be in contact with biological material will be formed on a first surface F1 of the bottom electrode 201.

Figure 3:
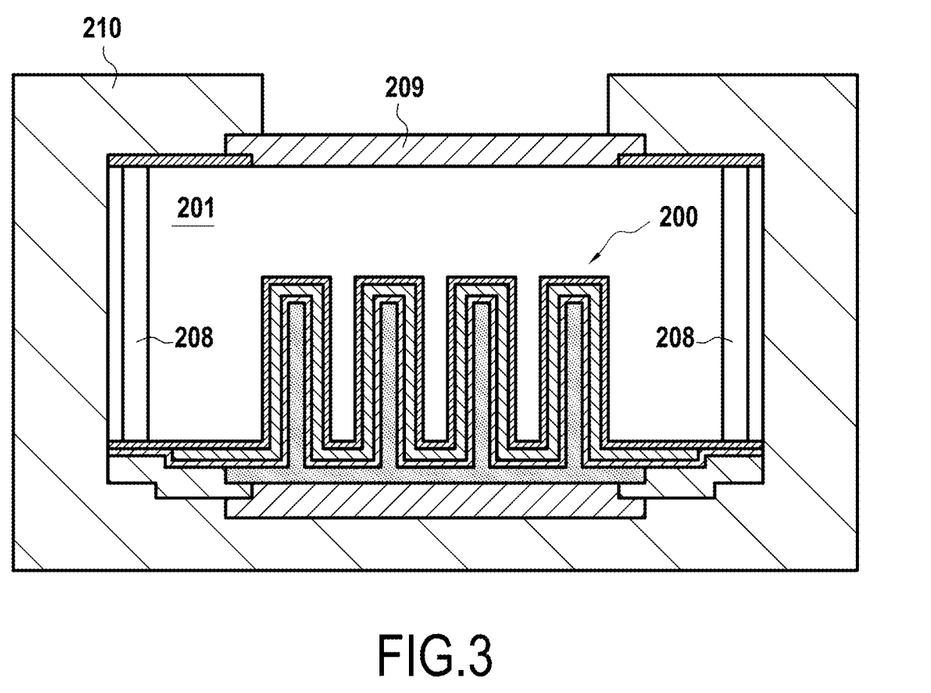
FIG. 3 is a side view of the two capacitors with the electrode formed.

FIG. 3 shows the stacked capacitors 200 of FIG. 2 after a step of forming trenches 208 which further delimits the bottom electrode 201. In this example, the trenches 208 are formed in the entire thickness of the bottom electrode 201, and these trenches may be filled with insulating material such as silicon dioxide.

On the bottom electrode 201, an electrode configured to be in contact with biological tissue is formed on the first surface F1 by depositing a layer of biocompatible conductive material forming an electrode 209.

The electrode 209 has a thickness of the order of a few micrometers and it may comprise a conductive material chosen in the group gold, nickel, tungsten, platinum, palladium, cobalt, or an alloy of at least two materials of the group of conductive materials.

In addition to the passivation layer 207 and the trenches 208, an additional encapsulating layer 210 is formed so as encapsulate the capacitor and to leave uncovered at least the electrode configured to be in contact with biological tissue 209.

It should be noted that if the device comprises separate components such as an electronic circuit, then the encapsulation may only concern the capacitor.

The thickness of the encapsulating layer 210 may be, by way of example, of the order of 10 micrometers.

Also, the encapsulating layer comprises an insulating material chosen in the group comprising alumina, parylene, or a combination of at least two materials of the group of insulating material.

As can be observed on the figure, the capacitor and the electrode configured to be in contact with biological tissue are in direct contact, and this improves the security of the device.

Figure 4:
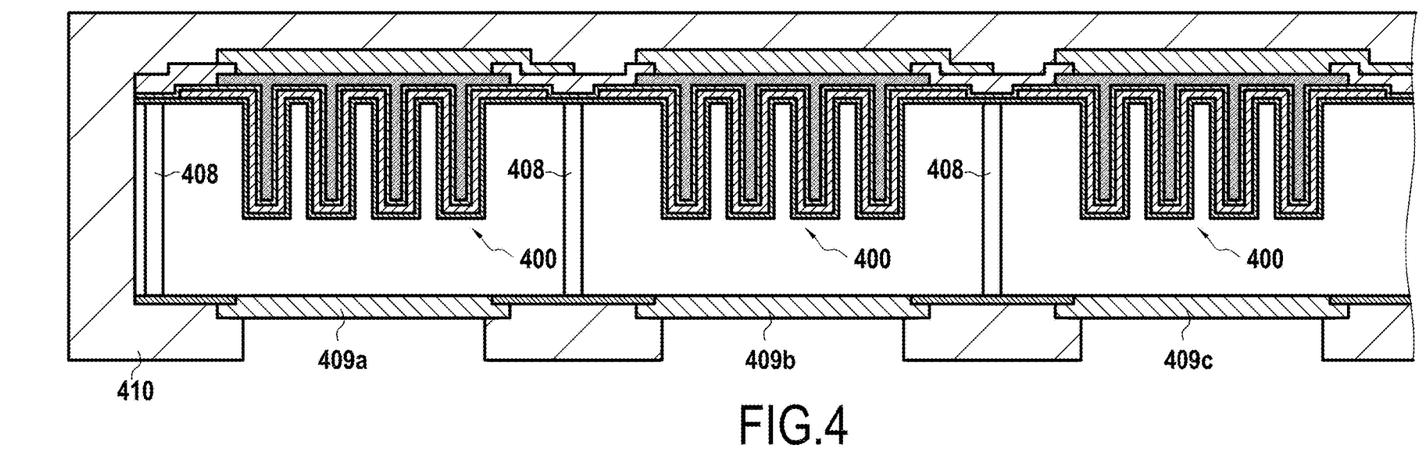
FIG. 4 is a side view of an array of capacitors and electrodes.

On FIG. 4, a side view of an array of capacitors and electrodes is represented. The capacitors are stacked capacitors 400 analogous to the stacked capacitors 200 described in reference to FIGS. 2 and 3.

Also, the capacitors 400 are separated by trenches 408 analogous to the trenches 208 described in reference to FIGS. 2 and 3.

Three electrodes configured to be in contact with biological tissue are shown on the figure, electrodes 409a, 409b, and 409c (analogous to the electrode 209 of FIG. 3). It should be noted that the array may comprise a larger number of electrodes 409i (with I being an index differentiating the electrodes). For example, the array may be a matrix of N times M electrodes. Therefore, the array extends in the direction perpendicular to the view.

The pitch (for example the distance between consecutive trenches) between the electrodes 409i may be of the order of at least 500 micrometres, so as to obtain capacitors having a large enough capacitance value (of the order of a nanofarad).

Figure 5:
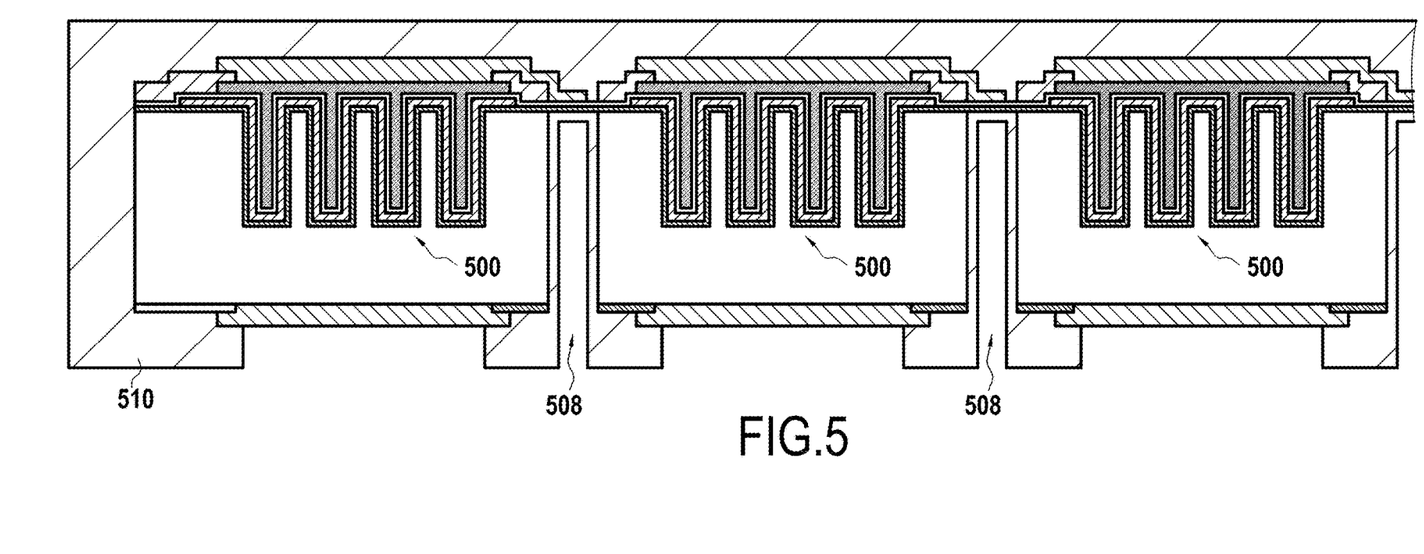
FIG. 5 is a side view of an alternative array of capacitors and electrodes.

An alternative array is shown on FIG. 5. In this example, trenches 508 are formed between stacked capacitors and these trenches remain filled with void, empty.

An encapsulating layer 510 (analogous to the encapsulating layer 210 of FIG. 3) is also deposited at the bottom and on the walls of the trenches, while still leaving an empty region in the trenches 510. In fact, the thickness of the encapsulating layer may be lower on the walls of the trenches 508 so as to maintain the presence of void.

The widths of the trenches may be of the order of 10 micrometres.

The embodiment of FIG. 5 allows obtaining a flexible array, which may be arranged on a non-planar surface.

Figure 6:
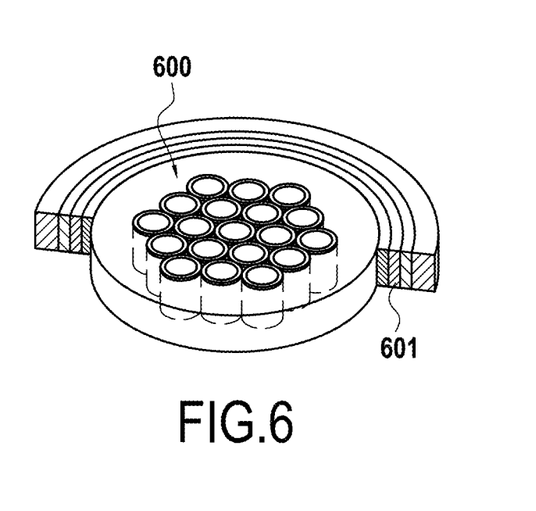
FIG. 6 is a perspective view of an example of capacitor and electrode.

FIG. 6 is a perspective view of an example of capacitor and electrode. More precisely, on this figure, an array of pillars 600 of a three-dimensional capacitor is shown. The electrode configured to be in contact with biological tissue is placed below and cannot be seen on the figure.

A circular insulation trench 601 is formed around the capacitor and electrode, but it should be noted that this additional insulation is not necessary when also using void/empty trenches between adjacent capacitors and electrodes.

Figure 7:
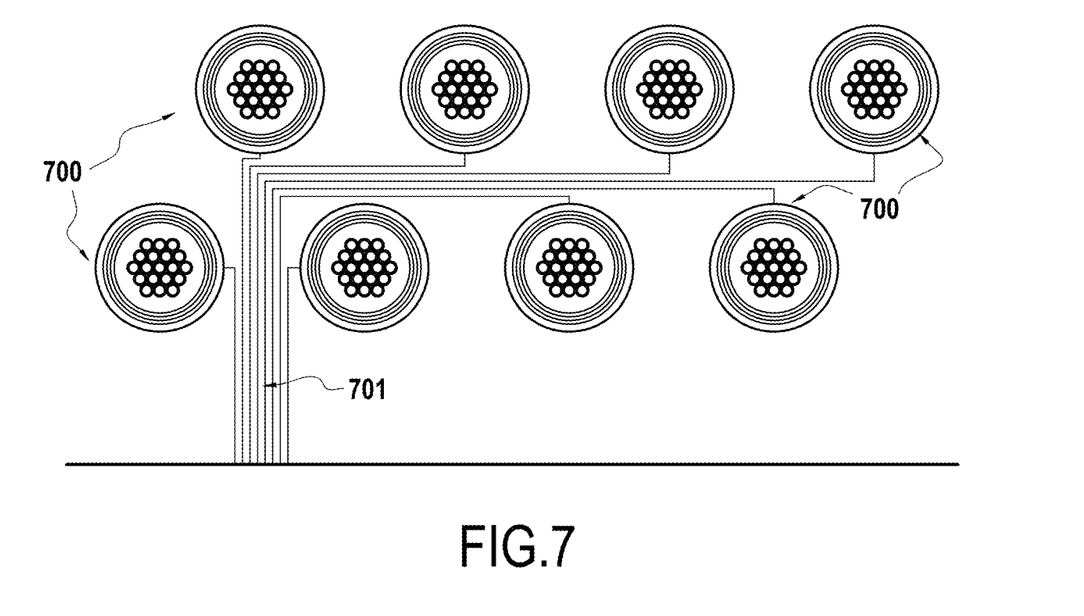
FIG. 7 shows another array of capacitors and electrodes.

FIG. 7 shows an example of array of capacitors and electrodes 700 similar to the one described in reference to FIG. 6. As can be seen on the figure, the capacitors and electrodes are separated: void is used to separate the capacitors and electrodes.

On the figure, metal lines 701 used to control the capacitors and electrodes or to receive the signals sensed by the electrodes are shown.

Figure 8:
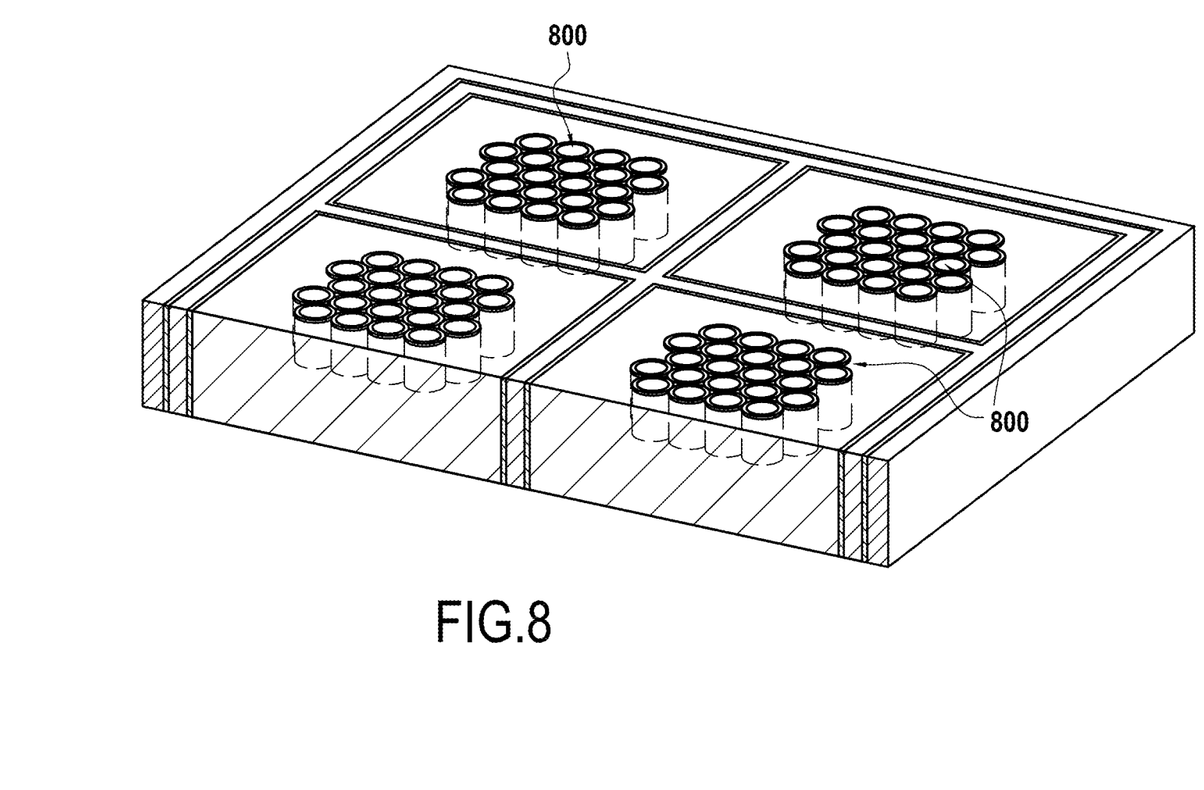
FIG. 8 is a perspective view of an array of capacitors and electrodes.

Various shapes may be used, for example, on FIG. 8, a rectangular matric arrangement of capacitors and electrodes 800 is shown.

Although the present invention has been described above with reference to certain specific embodiments, it will be understood that the invention is not limited by the particularities of the specific embodiments. Numerous variations, modifications and developments may be made in the above-described embodiments within the scope of the appended claims.

The invention claimed is:

1. An implementable semiconductor device, comprising:
   an electrode configured to be in contact with biological tissue and at least one capacitor,
   wherein the at least one capacitor comprises a capacitor electrode having a first surface facing and in direct contact with the electrode that is configured to be in contact with biological tissue, and
   wherein the at least one capacitor is a three-dimensional capacitor and the capacitor electrode comprises at least one of a pillar, a trench, or a hole, that is disposed on a side opposite to a side having the first surface facing and in direct contact with the electrode.

2. The implementable semiconductor device according to claim 1, wherein the electrode configured to be in contact with biological tissue comprises a layer of biocompatible conductive material facing said first surface of the capacitor electrode.

3. The implementable semiconductor device according to claim 1, wherein said capacitor electrode comprises a semiconductor region.

4. The implementable semiconductor device according to claim 1, wherein the electrode configured to be in contact with biological tissue comprises a conductive material chosen in the group comprising gold, nickel, tungsten, platinum, palladium, cobalt, or an alloy of at least two materials of the group of conductive materials.

5. The implementable semiconductor device according to claim 1, further comprising:
   an encapsulating layer comprising an insulating material chosen in the group comprising alumina, parylene, or a combination of at least two materials of the group of insulating material,
   wherein the encapsulating layer is arranged to at least partially encapsulate the at least one capacitor and to leave uncovered at least the electrode configured to be in contact with biological tissue.

6. The implementable semiconductor device according to claim 1, further comprising:
   a plurality of electrodes configured to be in contact with biological tissue,
   wherein each electrode configured to be in contact with biological tissue is associated with at least one capacitor comprising a capacitor electrode having a first surface facing and in direct contact with the electrode that is configured to be in contact with biological tissue.

7. The implementable semiconductor device according to claim 6, further comprising trenches surrounding each electrode configured to be in contact with biological tissue and their associated at least one associated capacitor.

8. The implementable semiconductor device according to claim 7, wherein the trenches are empty or comprise an insulating material.

9. A method for manufacturing an implementable semiconductor device, comprising:
   forming at least one capacitor comprising a capacitor electrode having a first surface;
   forming an electrode configured to be in contact with biological tissue and that is facing and in direct contact with the first surface of the capacitor electrode,
   wherein the at least one capacitor is formed to be a three-dimensional capacitor and the capacitor electrode is formed to comprise at least one of a pillar, a trench, or a hole, that is disposed on a side opposite to a side having the first surface facing and in direct contact with the electrode.

10. The method according to claim 9, further comprising depositing a layer of biocompatible conductive material on said first surface of the capacitor electrode.

11. The method according to claim 9, wherein the capacitor electrode comprises a semiconductor region.

12. The method according to claim 9, wherein forming the electrode configured to be in contact with biological tissue comprises depositing a layer of conductive material chosen in the group comprising gold, nickel, tungsten, platinum, palladium, cobalt, or an alloy of at least two materials of the group of conductive materials.

13. The method according to claim 9, further comprising:
forming an encapsulating layer comprising an insulating material chosen in the group comprising alumina, parylene, or a combination of at least two materials of the group of insulating material; and
arranging the encapsulating layer to at least partially encapsulate the capacitor and to leave uncovered at least the electrode configured to be in contact with biological tissue.

14. The method according to claim 9, further comprising:
forming a plurality of electrodes configured to be in contact with biological tissue,
wherein each electrode configured to be in contact with biological tissue is associated with at least one capacitor comprising a capacitor electrode having a first surface facing and in direct contact with the electrode configured to be in contact with biological tissue.

15. The method according to claim 14, further comprising forming trenches surrounding each electrode configured to be in contact with biological tissue and their associated at least one associated capacitor.

16. The method according to claim 15, wherein the trenches comprise an insulating material or are empty.

* * * * *